United States Patent [19]
Osborne

[11] Patent Number: 5,251,640
[45] Date of Patent: Oct. 12, 1993

[54] COMPOSITE WIRE GUIDE SHAFT

[75] Inventor: Thomas A. Osborne, Bloomington, Ind.

[73] Assignee: Cook, Incorporated, Bloomington, Ind.

[21] Appl. No.: 861,428

[22] Filed: Mar. 31, 1992

[51] Int. Cl.⁵ .............................................. A61B 5/00
[52] U.S. Cl. ...................................... 128/772; 604/95
[58] Field of Search ................ 128/657, 772; 604/95, 604/164, 280–282

[56] References Cited

U.S. PATENT DOCUMENTS

| | | |
|---|---|---|
| 2,573,361 | 10/1951 | Rodgers, Jr. et al. . |
| 2,749,643 | 6/1956 | Scott . |
| 3,421,247 | 1/1969 | Hubbard . |
| 3,684,605 | 8/1972 | Zwart . |
| 3,773,034 | 11/1973 | Burns et al. .......................... 128/657 |
| 3,924,632 | 12/1975 | Cook . |
| 3,953,637 | 4/1976 | Phillips . |
| 4,020,829 | 3/1977 | Willson et al. ........................ 604/95 |
| 4,061,806 | 12/1977 | Lindler et al. . |
| 4,178,713 | 12/1979 | Higuchi . |
| 4,215,703 | 8/1980 | Willson ................................. 604/95 |
| 4,425,919 | 1/1984 | Alston et al. ........................ 604/282 |
| 4,685,241 | 8/1987 | Foote et al. . |
| 4,690,175 | 9/1987 | Ouchi et al. . |
| 4,759,147 | 7/1988 | Pirazzini . |
| 4,817,613 | 4/1989 | Jaraczewski et al. . |
| 4,860,481 | 8/1989 | Christenson . |
| 4,885,865 | 12/1989 | Rumbaugh . |
| 4,981,478 | 1/1991 | Evard et al. ......................... 128/772 |
| 5,037,404 | 8/1991 | Gold et al. . |
| 5,057,092 | 10/1981 | Webster ............................... 604/282 |
| 5,095,915 | 3/1992 | Engleson ............................. 128/772 |

FOREIGN PATENT DOCUMENTS 0359549  3/1990  European Pat. Off. .

Primary Examiner—Max Hindenburg
Attorney, Agent, or Firm—Woodard, Emhardt, Naughton, Moriarty & McNett

[57] ABSTRACT

A composite wire guide shaft includes first and second sets of fibers which are arranged along a longitudinal axis and are embedded in an epoxy matrix. The first set of fibers are arranged substantially parallel to the longitudinal axis of the wire guide shaft and the remaining second set of fibers are helically wound in opposing directions about the longitudinal axis. The longitudinally parallel fibers provide pushability to the wire guide shaft while the helically wound fibers provide rotational stiffness for improved torqueability.

10 Claims, 4 Drawing Sheets

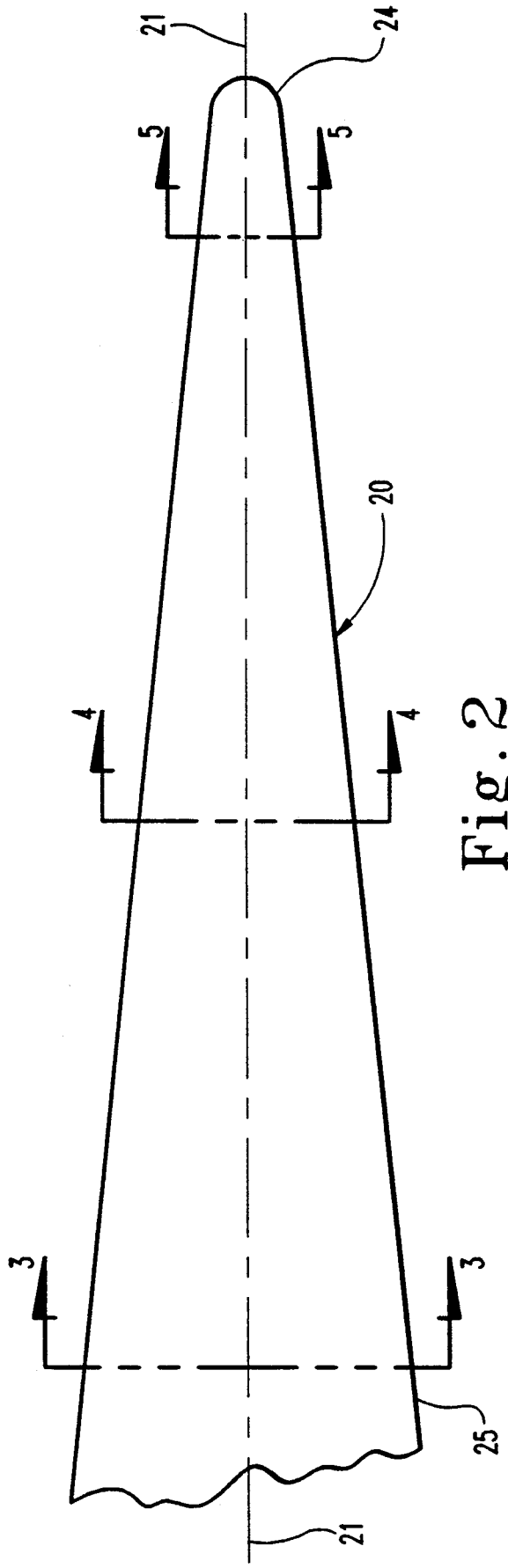
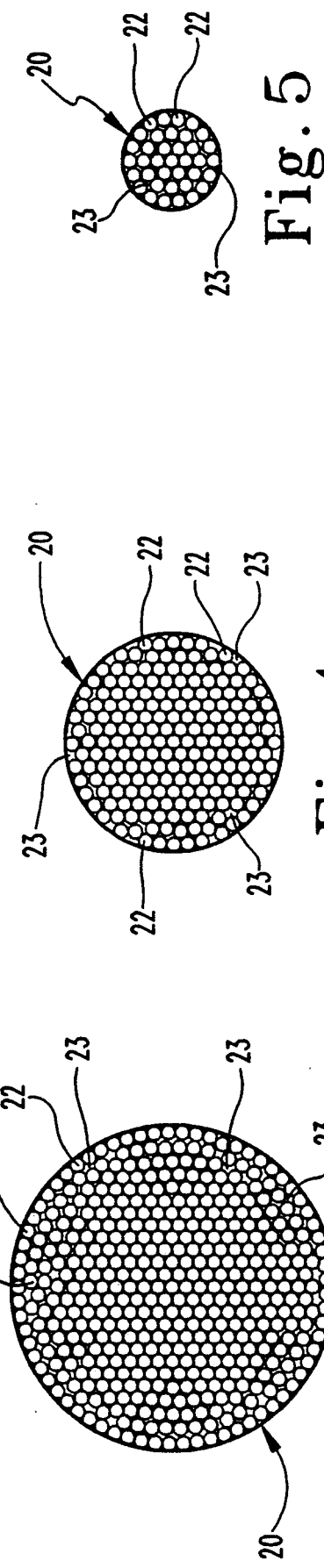
Fig. 2
Fig. 3
Fig. 4
Fig. 5

COMPOSITE WIRE GUIDE SHAFT

BACKGROUND OF THE INVENTION

Generally, the usefulness of a given wire guide can be judged based upon several performance and dimensional characteristics. Often these performance and dimensional characteristics are mutually contradictory. For instance, one characteristic that is desired in all wire guides is pushability or kink resistance. However, it is also desirable that the wire guide have good flexibility characteristics, especially at its distal end so that the guide can adapt to curved passageways in a patient without causing potential trauma by possibly puncturing a vessel wall. It is often necessary to sacrifice one performance characteristic in favor of another when constructing wire guides due to inherent limits of the metallic materials usually used for making wire guides.

Another important characteristic of wire guides is often referred to as its torque-ability or steerability. This characteristic refers to the ability of the wire guide to transfer a torque in a one-to-one relationship from the proximal end to the distal end of the wire guide without a whipping effect caused by a torque build-up in the wire guide. Depending upon the materials used to construct the wire guide shaft, the above three characteristics are all coupled to one extent or another. In other words, an increase in torque-ability of a given wire guide often results in decreased flexibility and/or pushability in the wire guide.

One dimensional characteristic that is intimately related to the above performance characteristics is the diameter of the wire guide. It is usually always desirable to have the smallest possible diameter for the wire guide. However, most if not all materials used to construct wire guides have thresholds below which the diameter of the wire guide cannot be decreased without completely sacrificing one or more of the guide's performance characteristics.

What is needed is a compositely constructed wire guide shaft which affords some independent control over the various performance and dimensional characteristics of the wire guide to an extent previously not possible with the materials and structures taught in wire guides of the prior art.

SUMMARY OF THE INVENTION

A composite wire guide shaft according to one embodiment of the present invention comprises a first set of fibers which are helically wound about a longitudinal axis and a second set of fibers which are are arranged substantially parallel to the longitudinal axis in an adjoining relationship to the first set of fibers. Both the first set of fibers and the second set of fibers are embedded in an adhesive matrix.

One object of the present invention is to provide an improved composite wire guide shaft.

Related objects and advantages of the present invention will be apparent from the following description.

BRIEF DESCRIPTION OF THE DRAWINGS

FIG. 2 is a partial side elevational view of a tapered composite core for a composite wire guide shaft according to one aspect of the present invention.

FIG. 3 is a cross section of the composite core of FIG. 2 taken along section 3—3.

FIG. 4 is a cross section of the composite core of FIG. 2 taken along section 4—4.

FIG. 5 is a cross section of the composite core of FIG. 2 taken along section line 5—5.

DESCRIPTION OF THE PREFERRED EMBODIMENT

Figure 1:
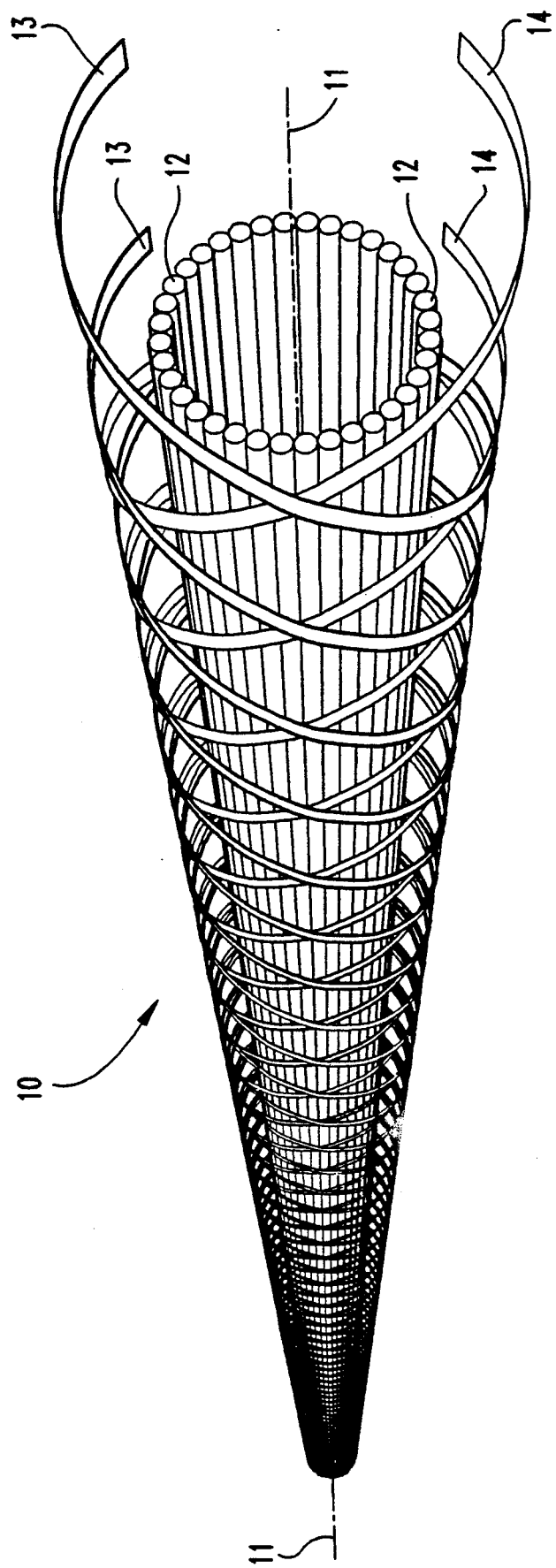
FIG. 1 is a sectioned perspective view of the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, there is shown a composite wire guide shaft 10 according to the preferred embodiment of the present invention. Shaft 10 includes a first set of fibers 12 which are arranged substantially parallel to the longitudinal axis 11 defined by the shaft, and a second set of fibers 13 and 14 which are helically wound about longitudinal axis 11. Fibers 12, 13 and 14 are all preferably held together by being embedded in an adhesive matrix, such as epoxy. Fibers 12 are arranged to define a cylinder such that the central core of the wire guide shaft is hollow in this case. Fibers 13 are helically wrapped around the cylinder defined by fibers 12 in a clockwise direction, while fibers 14 are wrapped around longitudinal axis 11 in a counterclockwise direction. All the fibers 12, 13 and 14 are bonded to one another by being embedded in an adhesive matrix such that the tiny spaces between the respective fibers are substantially filled with the adhesive.

It is believed that the fibers 12, which are arranged parallel to the longitudinal axis 11, are the primary determinants of the pushability characteristics of the wire guide shaft. The arrangement of the helically wound fibers 13 and 14 is believed to be the primary influencing factors on the torqueability performance characteristics of the wire guide shaft. These two performance characteristics are substantially decoupled in the structure shown in FIG. 1. For instance, the pushability of the wire guide could be altered by either increasing or decreasing the number of fibers 12 without significantly altering the torqueability characteristics of the wire guide shaft 10. On the other hand, the torqueability characteristics of the wire guide shaft can be varied substantially by changing the arrangement of the helically wound fibers 13 and 14. For instance, the helix angle of fibers 13 and 14 could be varied in order to change the torqueability characteristics of the wire guide shaft 10, or further layers of helically wound fibers could be added to further strengthen the torqueability characteristics.

The flexibility characteristics of the wire guide shaft 10 are believed to be intimately related to the arrangement of all the fibers 12, 13, and 14, the materials used for the respective fibers, the density ratio of fibers to epoxy, and finally, by the diameter of the shaft 10. As can be readily imagined, wire guide shafts could be made with significantly different performance characteristics based upon different arrangements, different fiber materials and different adhesives without altering the basic structure shown in FIG. 1. For instance, the fibers could be wrapped in alternating layers in opposite directions so as to impart good torque control characteristics to the finished shaft.

FIG. 2 shows a tapered composite core 20 according to another aspect of the present invention. Central core 20 illustrates one way in which the flexibility and pushability characteristics of a composite wire guide shaft can be varied along the length of the wire guide. The taper of central core 20 is achieved by including several composite fibers 22 of staggered lengths that are bunched together and embedded in epoxy matrix 23. As is readily apparent, the proximal portion 25 of central core 20 would be significantly less flexible than the small-diameter distal portion 24. Cross sections 3, 4 and 5 are included to show that the ratio of epoxy 23 to fibers 22 remains substantially constant along the length of central core 20. It being understood that the performance characteristics of the central core 20 could be further varied by varying the relative density of fibers to epoxy along the length of central core 20. Central core 20 could be completed into a composite wire guide shaft by helically winding a second set of fibers about longitudinal axis 21 in order to give the completed wire guide good torqueability characteristics.

Figure 6:
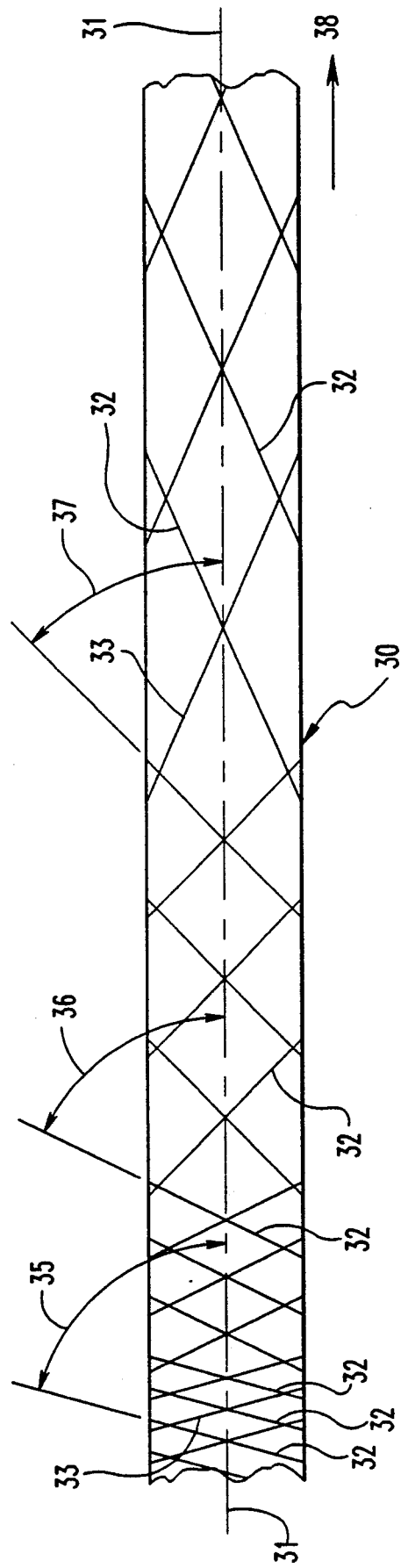
FIG. 6 is a partial side elevational view of a composite wire guide shaft according to another embodiment of the present invention.

FIG. 6 shows a composite wire guide shaft 30 according to another embodiment of the present invention in which the helix angle of the helically wound fibers varies along the length of the shaft in order to vary the torqueability characteristics along the length of the shaft. In particular, the torqueability characteristics are shown to decrease in the direction of the distal end 38 of the wire guide shaft 30. Wire guide shaft 30 includes a longitudinal axis 31 about which fibers 32 are helically wrapped in a clockwise direction and fibers 33 are helically wound around axis 31 in a counterclockwise direction. It is believed that a high helix angle such as 35 toward the proximal end of the wire guide shaft provides increased rotational stiffness. A medium helix angle 36 toward the center of the wire guide shaft provides less rotational stiffness because less rotational stiffness is needed as one progresses from the proximal to the distal end 38 of wire guide shaft 30. Finally, helix angle 37 toward tile distal end 38 of the wire guide shaft is substantially smaller because less rotational rigidity is needed at the extreme distal end of the wire guide shaft.

Figure 7:
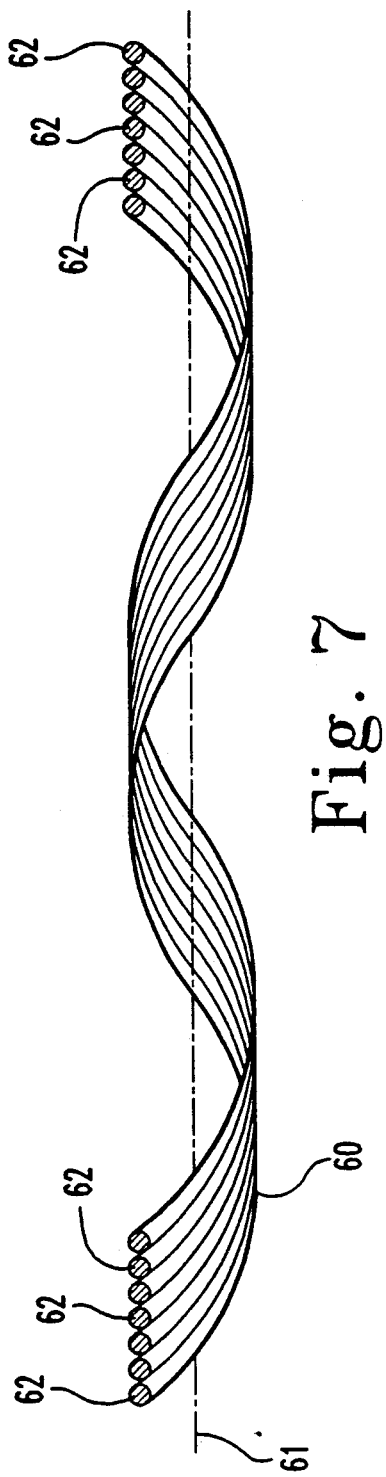
FIG. 7 illustrates another aspect of the present invention in which several fibers are joined together in a band and helically wrapped around a longitudinal axis.

FIG. 7 shows another aspect of the present invention in which a plurality of fibers 62 are grouped together to define a band 60 which is itself helically wound about a central axis 61. Such a helical winding could be substituted for either the fibers 13 or 14 shown in FIG. 1. The helix angle defined by band 60 could also be varied in the manner shown in FIG. 6 to vary the torsional characteristics of the composite wire guide shaft. Finally, a second band (not shown) could be cross-wound in the opposite direction as the band 60 shown in FIG. 7 in order that the completed wire guide shaft would have substantially equal torqueability characteristics in both clockwise and counterclockwise rotational directions.

Several other variations to the composite wire guide shaft of the present invention include but are not limited to winding the fibers in layers, including longitudinally parallel fibers outside the helically wound fibers or possibly interweaving the cross-wound fibers in some fashion.

Several different types of materials are contemplated for use in the fibers of the present invention. Among these are boron fibers, carbon or graphite fibers, polymeric aromatic nylon fibers (Kevlar ®), silicon carbide filaments, or possibly even fiberglass. These fibers would preferably have a diameter in the range of 0.0001 inch to 0.005 inch. The flat band 60 sown in FIG. 7 is preferably made between 0.010 and 0.125 inch wide. Several different epoxy resins are contemplated for use in constructing the composite wire guide shafts of the present invention. Among these are epoxy resins, polyester resins, single component resin-type glues and cyanoacrylates. The percentage of adhesive to fibers in the composite wire guide shafts of the present invention is preferably on the order of 80% fibers, with the remainder being adhesive. There would likely be a higher percentage of fibers when cyanoacrylate is used as the adhesive matrix.

Wire guide shafts according to the present invention could be made with either a hollow central core as shown in FIG. 1 or with a solid central core that includes a fiber bundle as shown in FIG. 2. One way of constructing the hollow shaft wire guide is to begin with a mandrel which is formed from a soft malleable material. The fibers in the adhesive matrix are then assembled around the mandrel which is subsequently removed from the composite wire guide shaft after the adhesive cures. Because the mandrel is formed from a soft malleable material, it could be stretched by applying tension forces to the ends thus reducing its diameter uniformly along its length in order to remove it from the central core of the composite wire guide shaft. This would have the effect of pulling the mandrel away from the inner surface of the tubular shaft allowing it to be removed freely.

One way of making a composite wire guide shaft according to the present invention having a solid core bundle of fibers would be to construct a mandrel as shown in FIG. 2 consisting essentially of a bundle of fibers embedded in an epoxy matrix. The outer layers of fibers are then mounted and wrapped about the central core and the adhesive allowed to cure to complete the composite wire guide shaft. A composite wire guide shaft having a bundle core would be generally stiffer and more kink-resistant, as would be desired in a heavy duty type wire guide, or in the vicinity of the proximal end of a wire guide. A hollow core would be a little more flexible, which would be more desirable for guides used in superselective procedures. There is also the possibility of constructing composite wire guide shaft having a solid core at the proximal end and a hollow core in the distal portion of the wire guide in order to incorporate the advantages of both alternatives in the same wire guide shaft.

The curing process for constructing composite wire guide shafts according to the present invention would generally depend on the material chosen as the adhesive to bond the fibers together. Epoxy and polyester resins could be cured at ambient temperatures or at elevated temperatures. They could be cured in a vacuum to remove any trapped air from the adhesive matrix and-/or be cured under pressure to insure a uniform distribution of resin in the fibers. This pressure could be applied by wrapping the structure prior to curing with the strip of polyethylene, Teflon ® or other suitable material that could be removed after the curing process. Alternatively, the wrap could also become a permanent part of the structure.

Pressure could also be applied prior to curing by shrinking a polyethylene, Teflon ®, nylon, or other suitable shrinkable sleeve over the structure. Such a sleeve would provide the wire guide shaft with a more compatible interface between blood and the fibers, and prevent fiber fragments from getting into the bloodstream should the shaft ever break during use. The sleeve would also give the shaft a lower coefficient of friction and/or serve as a base for hydrophylic, anti-throinbogenic and/or antibiotic coatings. The outer coating could be a fluorocarbon, polyeurethane, polyvinyl or any other suitable coatings which are well known in the art.

There are also other structural variations which could be incorporated into a composite wire guide shaft in order to vary the performance characteristics of the wire guide. For instance, in addition to employing an adhesive material used alone, the matrix could be mixed with short chopped fibers to give it added strength. Preferably, these small chopped fibers would be on the order of 0.0001 inch diameter up to about 0.020 inch long. Another alternative would be to mix different types of fibers in one shaft. For example, less expensive glass fibers could be used in the core of the shaft to give it good longitudinal stability, while more expensive carbon fibers could be wrapped around the outside to give the shaft good torque transmittance.

Figure 8:
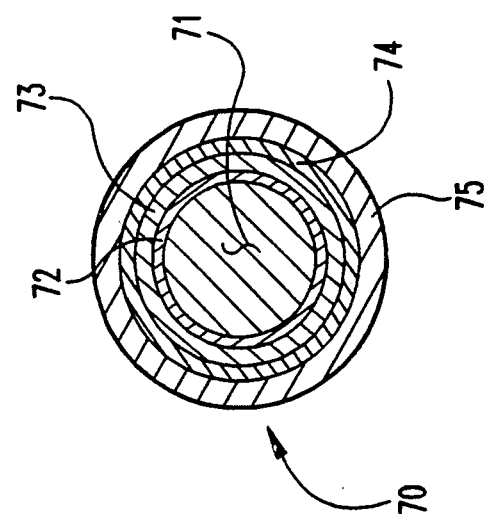
FIG. 8 is a cross-sectional view of a composite wire guide shaft according to another aspect of the present invention.

The present invention also contemplates various hybrid structures in which a metallic mandrel of the types well known in the art is included as a central core about which groups of fibers are attached and/or wrapped around the mandrel and then embedded in an epoxy matrix. A cross-section of such a hybrid is shown in FIG. 8. In this case, shaft 70 includes a nitinol central core 71, concentrically surrounded by fiber layers 72 and 73, which are embedded in an epoxy matrix. Layer 73 is surrounded by a polyethylene sleeve 74 and a hydrophilic coating 75. In this example, a nitinol core would add to the structure's ability to tranmit torque by resisting the adhesive matrix's tendency to take a set or develop a curved cast when stored in a coiled form. Also, in another hybrid alternative, platinum could be incorporated into the structure in order to enhance radiopacity by either including a platinum coil oil the outer surface of the shaft or by incorporating a platinum mandrel as at least a portion of the central core of the shaft.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A composite wire guide shaft comprising:
   first fibers helically wound about a longitudinal axis;
   second fibers arranged substantially parallel to said longitudinal axis adjoining said first fibers;
   said first fibers and said second fibers being embedded in an adhesive matrix; and
   said first fibers and said second fibers being a majority of the weight of the wire guide shaft.

2. The composite wire guide shaft of claim 1 wherein a portion of said first fibers are wound about said longitudinal axis in a clockwise direction and the remaining portion of said first fibers are wound about said longitudinal axis in a counterclockwise direction.

3. The composite wire guide shaft of claim 2 wherein said first fibers and said second fibers are chosen from a group consisting of boron fibers, carbon fibers, fiberglass, polymeric aromatic nylon fibers, or silicon carbide filaments.

4. The composite wire guide shaft of claim 3 having a hollow central core substantially coaxial with said longitudinal axis; and
   said first fibers and said second fibers surround said hollow central core.

5. The composite wire guide shaft of claim 3 further comprising a central core substantially coaxial with said longitudinal axis which includes a bundle of third fibers; and
   said first fibers and said second fibers surround said bundle of third fibers.

6. The composite wire guide shaft of claim 5 wherein said third fibers are chosen from a group consisting of boron fibers, carbon fibers, fiberglass, polymeric aromatic nylon fibers, or silicon carbide filaments.

7. The composite wire guide shaft of claim 6 wherein said bundle of third fibers is embedded in an adhesive matrix.

8. The composite wire guide shaft of claim 3 wherein said first fibers are wound in a plurality of layers.

9. The composite wire guide shaft of claim 3 wherein said second fibers are side by side and arranged to define a cylinder substantially coaxial with said longitudinal axis.

10. The composite wire guide shaft of claim 3 having a tapering cross section along a portion of the shaft.

* * * * *

UNITED STATES PATENT AND TRADEMARK OFFICE
CERTIFICATE OF CORRECTION

PATENT NO. : 5,251,640
DATED      : October 12, 1993
INVENTOR(S) : Thomas A. Osborne It is certified that error appears in the above-indentified patent and that said Letters Patent is hereby corrected as shown below:

On the title page, please change Assignee to read --Cook Incorporated--.

Column 3, line 53, delete the word "tile" and insert the word --the--.

Column 4, line 13, after the number 60, delete the word "sown" and substitute the word --shown--.

Column 5, lines 15 and 16, delete the word "antithroinbogenic" and substitute the word --antithrombogenic--.

Column 5, line 51, after the word "coil", delete the word "oil" and insert the word --on--.

Signed and Sealed this

Tenth Day of May, 1994

Attest:

BRUCE LEHMAN

*Attesting Officer*    *Commissioner of Patents and Trademarks*